(12) United States Patent
Frigoli et al.

(10) Patent No.: US 6,312,811 B1
(45) Date of Patent: Nov. 6, 2001

(54) PHOTOCHROMIC NAPHTHO [2,1-B]PYRAN COMPOUNDS CONTAINING BITHIENYL OR TERTHIENYL SUBSTITUENTS, PROCESS FOR THEIR MANUFACTURE, AND PHOTOCHROMIC MATERIALS AND ARTICLES OBTAINED

(75) Inventors: Michel Frigoli, Marseille; Nicole Rebiere-Galy, Paris; Corinne Moustrou, Marseille; Andre Samat, Marseille; Robert Guglielmetti, Marseille, all of (FR)

(73) Assignee: Essilor International Compagnie Generale d'Optique, Charenton Cedex (FR)

( * ) Notice: Subject to any disclaimer, the term of this patent is extended or adjusted under 35 U.S.C. 154(b) by 0 days.

(21) Appl. No.: 09/349,686

(22) Filed: Jul. 8, 1999

(51) Int. Cl.$^7$ ............... C03C 4/06; C07D 407/14; C07D 409/14; C07D 409/04

(52) U.S. Cl. .............. 428/411.1; 52/204.5; 296/84.1; 296/146.1; 501/13; 548/525; 548/527; 549/59

(58) Field of Search ................. 548/525, 527; 549/59; 428/411.1, 412, 426, 913; 52/204.5; 296/84.1, 146.1; 501/13

(56) References Cited

U.S. PATENT DOCUMENTS 5,543,533 * 8/1996 Allegrini et al. .................. 549/389

OTHER PUBLICATIONS

Rebiere–Galy, English translation of portions of document previously submitted as Ref. C1, entitled "Synthese et caracterisation de nouveaux chromenes photochromiques lies a un motif thiophenique: application a des materiaux organiques conducteurs," Doctoral thesis, presented at the University of the Mediterranean at Marseilles, Jul. 10, 1998.

* cited by examiner

Primary Examiner—Paul Thibodeau
Assistant Examiner—Ramsey Zacharia
(74) Attorney, Agent, or Firm—Fulbright & Jaworski LLP

(57) ABSTRACT

The photochromic compounds of the invention correspond to the formula:

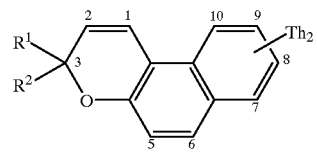

in which $Th_2$ represents a bithienyl group in one of the positions 5 to 10 of the naphthenic ring system system, $R^1$ denotes a bithienyl or trithienyl group and $R^2$ denotes a bithienyl, trithienyl, aryl, naphthyl, thienyl, furyl, pyrrolyl or N-alkylpyrrolyl group.

12 Claims, No Drawings

PHOTOCHROMIC NAPHTHO [2,1-B]PYRAN COMPOUNDS CONTAINING BITHIENYL OR TERTHIENYL SUBSTITUENTS, PROCESS FOR THEIR MANUFACTURE, AND PHOTOCHROMIC MATERIALS AND ARTICLES OBTAINED

The invention relates to photochromic compounds, more particularly heterocyclic compounds of the naphtho[2,1-b] pyran family substituted with bi- or terthienyl groups, and to their application in the field of materials and articles with variable optical transmission.

When photochromic compounds are subjected to irradiation containing ultraviolet rays (sunlight, xenon lamps or mercury lamps), they undergo a reversible color change. As soon as the excitation stops, they regain their original color.

In recent years, organic materials intended for optical applications have been the subject of considerable research. Ophthalmic glasses, glass for the construction industry, motor vehicle or airplane windshields and helmet visors, whose transparency in the visible range can be modified by using photochromic compounds, have particularly attracted attention. For this type of application using sunlight (heliochromism), the photochromic active compound must satisfy a certain number of criteria, among which are:

high colorability in the visible range after excitation with light (colorability is a measure of the capacity of a photochromic compound to exhibit an intense color);

an absence of coloration (or a weak coloration) in the initial state;

rapid kinetics of thermal decolorization at room temperature;

low decolorization with visible light; and a high speed of coloration.

One of the major difficulties encountered with photochromic compounds is that of obtaining a compromise between high colorability and rapid decolorization kinetics. The reason for this is that, under continuous solar irradiation, a photostationary equilibrium is established between the molecules which become colored under the action of ultraviolet light and those which become decolorized under the conjugate action of temperature and visible light. Thus, frequently, an increase in the rate of decolorization entails a decrease in the colorability.

The Applicant Company has discovered a novel family of naphtho[2,1-b]pyrans substituted with bithienyl or terthienyl groups, which have particularly advantageous photochromic properties.

The compounds in accordance with the invention have, compared with the naphtho[2,1-b]pyrans of the prior art, a colorability which is at least equivalent but higher coloration speeds and decolorization speeds. The following have also been found for these compounds:

an absence of coloration or only very weak coloration in the original state;

a particularly long life;

a sensitivity to low-energy ultraviolet rays (wavelengths greater than 380 nm);

an absorption of the colored forms at long wavelength (539 nm).

This combination of characteristics makes these novel compounds particularly advantageous for the manufacture of photochromic materials, in particular comprising a substrate made of transparent polymer material such as organic glasses with variable optical transmission (glass for sunglasses, glass for the construction industry, motor vehicle or airplane windshields, and riding or flying helmet visors).

The photochromic compounds can be incorporated directly into the organic glass substrate or dissolved in a polymer film stuck to the organic glass substrate.

The compounds which form the subject of the invention are [3H]naphtho[2,1-b]pyrans (I) comprising, on one of the positions 5 to 10, preferably position 8, of the naphthalene ring system, a bithienyl ($Th_2$) group and comprising in position 3 at least one ($Th_2$) group or at least one terthienyl ($Th_3$) group.

More particularly, the compounds of the invention correspond to the general formula below:

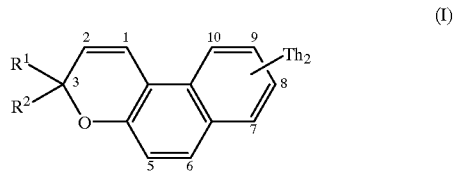

(I)

in which $Th_2$ is represented by formula (II):

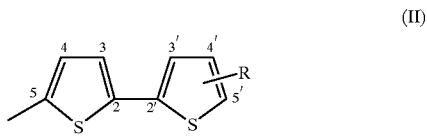

(II)

in which:

R denotes a substituent which can occupy one of the positions 3, 3', 4, 4' or 5', preferably position 5', and which is chosen from a hydrogen atom, an alkyl group, a cycloalkyl group, an aryl group, a group $OR^3$, $SR^3$, $COR^3$ or $COOR^3$ in which $R^3$ denotes a hydrogen atom, an alkyl or cycloalkyl group, an aryl group, an amino group, an $NO_2$, CN or SCN group, a halogen atom or a mono- or polyhaloalkyl group, $R^1$ denotes a $Th_2$ group as represented by formula (II) or a terthienyl ($Th_3$) group as represented by formula (III):

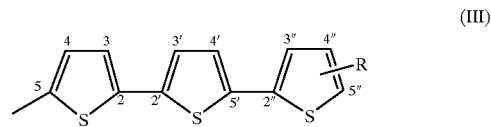

(III)

in which R is a substituent as denoted above in describing formula (II) and which can occupy one of the positions 3, 3', 3", 4, 4', 4", and 5", preferably position 5", and $R^2$ can be a $Th_2$ group as defined in formula (II), a $Th_3$ group as defined in formula (III), an aryl group, a naphthyl group, a thienyl group, a furyl group or a pyrrolyl or N-alkylpyrrolyl group.

In this definition of $R^2$, an aryl group denotes a phenyl, a phenyl which is mono- or polysubstituted with one (or more) alkyl, cycloalkyl, phenyl or amino substituents(s), a halogen, a group $OR^3$, $SR^3$, $COR^3$ or $COOR^3$ (in which $R^3$ has the same meaning as above); the groups $R^2$ of the naphthyl type can be substituted with the same substituents.

The heterocyclic groups (thiophene, furan, pyrrole) can be benzo-fused and the benzo group can bear alkyl, cycloalkyl, aryl, $OR^3$, $SR^3$, $COR^3$ or $COOR^3$ (in which $R^3$ has the same meaning as above), amino, $NO_2$, CN or SCN, or mono- (or poly-)haloalkyl substituents.

Preferably, $R^1$ represents a $Th_3$ group.

In the bithienyl and terthienyl substituents, the alkyl groups are preferably $C_1$–$C_6$ alkyl groups, for example methyl, ethyl, propyl, butyl, pentyl and hexyl; the cycloalkyl groups are $C_5$–$C_7$ cycloalkyl groups, for example cyclopentyl, cyclohexyl and cycloheptyl; the aryl groups denote a phenyl, a phenyl which is mono- or polysubstituted with one (or more) $C_1$–$C_6$ alkyl, $C_5$–$C_7$ cycloalkyl, phenyl and amino substituent(s); the halogens preferably represent Br, Cl and F; and the mono- (or poly-)haloalkyl groups are preferably mono-(or poly-)chloro or -fluoro $C_1$–$C_6$ alkyl groups, for example $CF_3$.

The compounds represented by formula (I) can be prepared by the coupling reaction of a suitably substituted propargyl alcohol (A) with a 2-naphthol bearing the bithienyl group (B) (Scheme 1).

This reaction is carried out in dichloromethane in the presence of an acid catalyst (PPTS: pyridinium para-tolueuesulfonate):

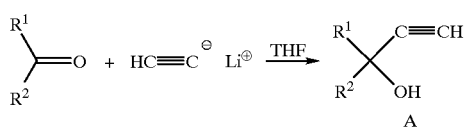

Scheme 1

The propargyl alcohols can be prepared as described in Scheme 2, by the action of lithium acetylide on a suitably substituted ketone.

Scheme 2

The naphthols (B) can be prepared in two different ways depending on whether the bithienyl group must occupy position 7 or the other positions (5, 6, 8–10) on the target molecule (I).

The preparation of 5-(2,2'-bithien-5-yl)-2-hydroxynaphthalene 6 (precursor of the naphthopyrans (I) substituted in position 7 with the $Th_2$ group) is carried out in four steps as indicated in Scheme 3. Bithienylmagnesium bromide 2 (obtained by a transmetallation reaction using 2,2'-bithiophene 1) reacts with 6-methoxy-1-tetralone (3) to give the derivative (4). After an oxidation reaction in the presence of chloranil (2, 3, 5, 6 -tetrachloro-1,4-benzoquinone), the resulting compound 5 is demethylated with boron tribromide in dichloromethane to give the expected naphthol 6.

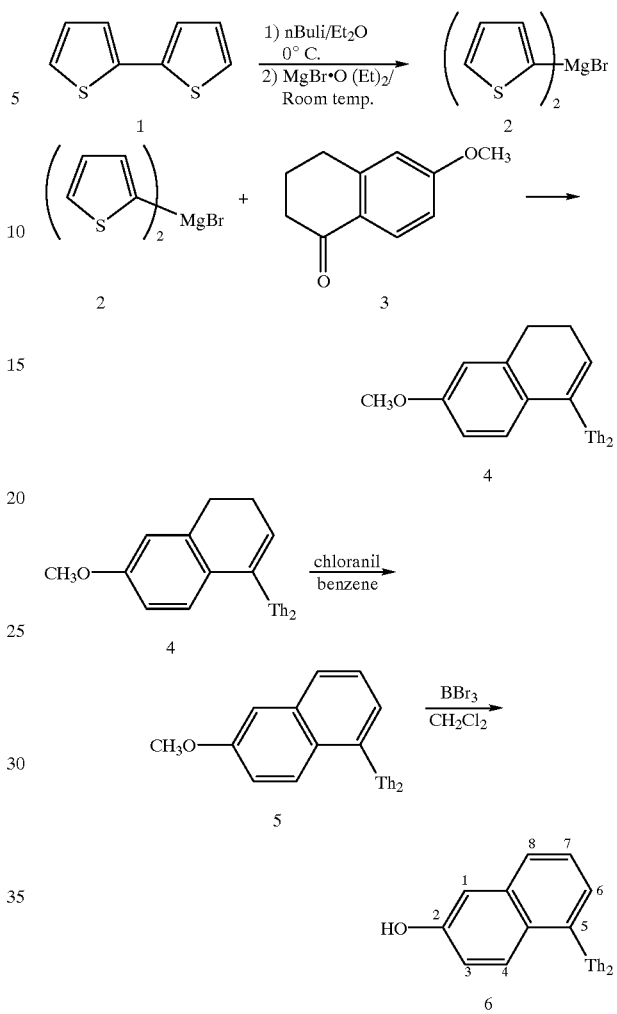

Scheme 3

The naphthols of the type 9 (which give access to the naphthopyrans of formula (I) substituted in positions 5, 6, 8, 9 or 10 with a $Th_2$ group) are prepared by a coupling reaction, catalyzed with a palladium catalyst such as Pd $(PPh_3)_4$, between the bithiophene boron derivative 7 and a bromo-2-naphthol (Scheme 4) or a 2-naphthol substituted with a triflate group, the bromine substituent or triflate group occupying one of positions 3, 4 or 6–8 of the naphthalene ring system.

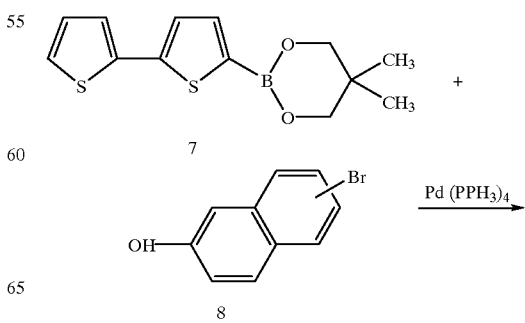

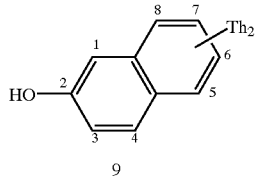

Scheme 4

The naphthopyrans of the present invention show particularly advantageous photochromic properties when compared with those of molecules of the same family of the prior art. A toluene solution of the compounds of formula (I) becomes colored and decolorizes very rapidly at room temperature. The main advantage of these novel compounds is that the rapid responses both in coloration and in decolorization do not entail a significant decrease in colorability, as might have been expected, and can sometimes even be accompanied by an increase therein.

Another advantage of the compounds in accordance with the invention is that they become colored under the action of ultraviolet rays with a wavelength of greater than 380 nm, whereas most of the similar compounds of the prior art become only slightly or not at all colored under the same conditions. This property makes it possible to use photochromic compounds of this type for the preparation of transparent articles made of organic glass that absorbs ultraviolet rays of shorter wavelengths (glass for the construction industry and airplane or motor vehicle windshields), in particular for the manufacture of glass for spectacles or for riding or flying helmet visors.

The compounds in accordance with the invention can be introduced directly into a transparent polymer matrix or can be incorporated into a composition intended to be applied onto a transparent organic polymer material. In this case, the compounds which are the subject of the invention are dissolved in a suitable solvent (for example chloroform, ethyl acetate, acetone, acetonitrile, dichloromethane or benzene) and incorporated into a solution of polymer (for example polyurethane, polyacrylate, polymethacrylate) in the same solvent.

The compositions are then applied in the form of a film a few micrometers thick on to a transparent polymer support (such as polycarbonate, cellulose acetate or polyalkyl acrylate), to obtain a photochromic material which can become colored in the presence of ultraviolet radiation and rapidly regains its non-colored and transparent state in the absence of a light source.

The compounds in accordance with the invention have the advantage of allowing this color change a large number of times at temperatures close to room temperature.

More specifically, the compounds in accordance with the invention may be introduced into a composition which is intended to be applied to or introduced into a transparent organic polymer material in order to obtain a transparent photochromic article. They may also be introduced into solid compositions such as plastic films, sheets and lenses in order to produce materials which may especially be used as ophthalmic lenses, sunglasses, visors, camera optical systems and filters, glass for the construction industry, airplane or motor vehicle windshields and helmet visors.

The liquid compositions which constitute one subject of the invention are essentially characterized in that they contain the compounds in accordance with the invention in dissolved or dispersed form in a solvent-based medium which are suitable for application to or introduction into a transparent polymer material.

Solvents which may more particularly be used are organic solvents chosen from benzene, toluene, chloroform, dichloromethane, ethyl acetate, methyl ethyl ketone, acetone, ethyl alcohol, methyl alcohol, acetonitrile, tetrahydrofuran, dioxane, ethylene glycol methyl ether, dimethylformamide, dimethyl sulfoxide, methylcellosolve, morpholine and ethylene glycol.

When the compounds in accordance with the invention are dispersed, the medium may also contain water.

According to another embodiment, the compounds in accordance with the invention may be introduced into, and preferably dissolved in, colorless or transparent solutions prepared from transparent polymers, transparent copolymers or mixtures of transparent polymers in a suitable organic solvent.

Among the polymers and copolymers which may be mentioned are polyurethanes, poly(meth)acrylates, polyallyl (meth)acrylates, cellulose derivatives such as nitrocellulose, cellulose acetate and ethylcellulose, polyvinyl chloride, polystyrene, poly(alkyl)styrene and polyvinylpyrrolidone.

Examples of such solutions are, inter alia, solutions of nitrocellulose in acetonitrile, of polyvinyl acetate in acetone, of polyvinyl chloride in methyl ethyl ketone, of polymethyl methacrylate in acetone, of cellulose acetate in dimethylformamide, of polyvinylpyrrolidone in acetonitrile, of polystyrene in benzene, and of ethylcellulose in methylene chloride.

These compositions may be applied to transparent supports, such as supports made of polyethylene glycol terephthalate, of borylated paper, or of cellulose triacetate, and dried in order to obtain a photochromic material, which may become colored in the presence of ultraviolet radiation and which returns to the colorless and transparent state in the absence of the source of radiation.

The photochromic compounds of the present invention, or the compositions containing them, which are defined above may be applied to or incorporated into a solid transparent polymerized organic material which is suitable for transparent articles such as ophthalmic lenses, or into useful materials for use in sunglasses, visors, camera optical systems and filters, glass for the construction industry, airplane or motor vehicle windshields and helmet visors.

By way of solid transparent materials which may be used to produce ophthalmic lenses in accordance with the invention, there may be mentioned polyol(allyl carbonate) polymers, polyacrylates, poly(alkyl acrylates) such as polymethyl methacrylates, cellulose acetate, cellulose triacetate, cellulose acetate propionate, cellulose acetate butyrate, poly (vinyl acetate), poly(vinyl alcohol), polyurethanes, polycarbonates, polyethylene terephthalates, polystyrenes, poly(styrene-methyl methacrylate)s, copolymers of styrene and acrylonitrile, and polyvinyl butyrates.

The transparent copolymers or mixtures of transparent polymers are also suitable for producing such materials.

There may be mentioned, in this respect, materials prepared from polycarbonates, such as poly(4,4'-dioxy-2,2-diphenylpropane), polymethyl methacrylate, polyol(allyl carbonate)s, in particular such as diethylene glycol bis(allyl carbonate) and the copolymers thereof, for example such as with vinyl acetate. The copolymers of diethylene glycol bis(allyl carbonate) and of vinyl acetate (80–90/10–20) may be mentioned in particular, and also the copolymer of diethylene glycol bis(allyl carbonate) with vinyl acetate, cellulose acetate and cellulose propionate, and cellulose butyrate (80–85/15–20).

The polyol(allyl carbonate)s are prepared using allyl carbonates of linear or branched, aliphatic or aromatic liquid polyols, such as aliphatic bis(allyl carbonate) glycols or alkylene bis(allyl carbonate)s. Among the polyol(allyl carbonate)s that can be used to prepare the solid transparent materials which may be used in accordance with the invention, there may be mentioned ethylene glycol bis(allyl carbonate), diethylene glycol bis(2-methallyl carbonate), diethylene glycol bis(allyl carbonate), ethylene glycol bis (2-chloroallyl carbonate), triethylene glycol bis(allyl carbonate), 1,3-propanediol bis(allyl carbonate), ropylene glycol bis(2-ethylallyl carbonate), 1,3-butanediol bis(allyl carbonate), 1,4-butanediol bis(2-bromoallyl carbonate), dipropylene glycol bis(allyl carbonate), trimethylene glycol bis(2-ethylallyl carbonate), pentamethylene glycol bis(allyl carbonate), and isopropylenebisphenol bis(allyl carbonate). The most important product consists of diethylene glycol bis(allyl carbonate), also known under the name CR39.

The amount of photochromic compounds to be used in accordance with the invention, either in the composition or at the time of its introduction into the solid support, is not critical and generally depends on the intensity of the color that the composition may impart to the material after exposure to radiation. Generally speaking, the more photochromic compounds are added, the more intense will be the coloration under irradiation.

In accordance with the invention, an amount is used which is sufficient to impart to the treated material the property of changing color at the time of exposure to radiation. This amount of photochromic compounds is generally between 0.01 and 20% by weight, and preferably between 0.05 and 10% by weight, relative to the total weight of the optical material or of the composition.

The photochromic compounds in accordance with the invention may also be introduced into a temporary transfer support (such as a varnish which forms a coating on a substrate) and then be thermally transferred into the substrate, as described in particular in U.S. Pat. No. 4,286,957 or 4,880,667.

These compounds can be used with other photochromic compounds, such as photochromic compounds which give rise to different colorations such as blue or green, and which are known in the prior art. Thus, spiro(indoline-oxazines), which are well known in the prior art, can be used.

The examples which follow are intended to illustrate the invention without, however, being limiting in nature.

In the examples, except where otherwise indicated, all the percentages and parts are expressed on a weight basis.

EXAMPLE 1

Synthesis of 3,7-bis(2,2'-bithien-5-yl)-3-(2-thien-yl)-[3H]-naphtho[2,1-b]pyran.

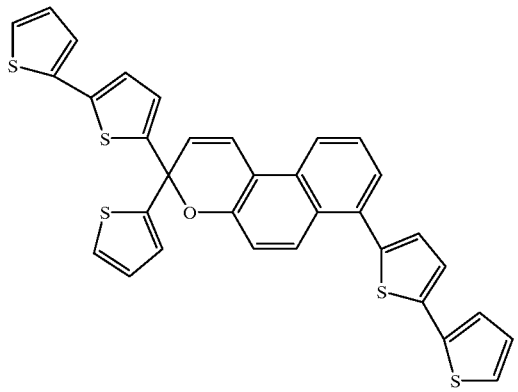

Step 1

0.072 mol of 2-bromothiophene and 2 g of [1,3-bis (diphenylphosphino)propane]dichloronickel (II) dissolved beforehand in 100 ml of anhydrous ethyl ether are introduced into a 250 ml 2-necked round-bottomed flask fitted with a stirring system and on which is mounted a condenser. The reaction medium is maintained under argon. Freshly prepared 2-thienylmagnesium bromide (0.072 mol) is added at 0° C., the addition lasting about 40 minutes. The reaction mixture is stirred for 3 hours. It is cooled in a bath of ice and an aqueous 10% sulfuric acid solution is added slowly until two clear phases are obtained. After separation of the phases by settling, the aqueous phase is extracted with ethyl ether (3×100 ml). The combined organic phases are dried over magnesium sulfate.

After evaporation of the solvent under reduced pressure, the crude product is purified by chromatography on a column of silica eluted with pure pentane.

The 2,2'-bithiophene is obtained in a yield of 95%.

Empirical formula: $C_8H_6S_2$

Molecular mass: 166.220

Melting point: 32° C.

Step 2

A mixture consisting of 6 mmol of 4-methoxybenzoyl chloride, 6 mmol of 2,2'-bithiophene prepared according to Step 1 and 15 ml of anhydrous benzene is cooled, under argon, using a bath of ice-water. 6 mmol of $SnCl_4$ are added slowly. The mixture is stirred for 30 minutes. The formation of a precipitate is observed, and 30 ml of benzene are added, followed by 15 ml of aqueous 10% hydrochloric acid solution. Once the dissolution of the precipitate is complete, the aqueous phase is extracted with benzene. The resulting organic phase is washed with water until a neutral pH is obtained, dried over magnesium sulfate and then concentrated under reduced pressure. The resulting (2,2'-bithien-5-yl) (2-thienyl) ketone is washed with pentane and then filtered.

Empirical formula: $C_{13}H_8S_3$

Molar mass: 276.404 g

Yield: 83%

Melting point: 98° C.

Step 3

A mixture consisting of lithium acetylide (15 mmol) and 200 ml of anhydrous THF is cooled to 0° C., under argon, using an ice-water bath. 1.5 mmol of the ketone prepared in Step 2 are then added in a single portion. After warming to room temperature, the reaction mixture is stirred for 3 hours. The reaction is monitored by thin layer chromatography on silica. The solution is then hydrolyzed with saturated aqueous ammonium chloride solution. The water/THF mixture is extracted with ethyl ether.

The resulting organic phases are combined, dried over magnesium sulfate and then concentrated under reduced pressure. The crude product is chromatographed on silica gel with pentane/dichloromethane mixtures of increasing polarity (50:50 to 0:100). The 1-(2,2'-bithien-5-yl)-1-(2-thienyl)-2-propyn-1-ol is isolated in the form of an oil.

Yield: 81%

Empirical formula: $C_{15}H_{10}OS_3$

Molar mass: 302.441.

Step 4

0.018 mol of bithiophene prepared in Step 3 dissolved in 90 ml of anhydrous ethyl ether is introduced into a 250 mol 3-necked round-bottomed flask fitted with a stirring system and over which is mounted a condenser. The reaction mixture is cooled to 0° C. and 0.021 mol of 1.6M n-butyllithium in hexane is added slowly.

The reaction is carried out under argon. After one hour, 0.018 mol of $MgBr.O(Et)_2$ is added to the lithiated derivative.

The reaction mixture is left for two hours at room temperature, after which 18 mmol of 6-methoxy-1-tetralone dissolved beforehand in 15 ml of anhydrous ether are added. The mixture is maintained at the reflux temperature of the ethyl ether for 5 hours. The reaction mixture is allowed to return to room temperature and is then cooled (ice bath). Aqueous 10% sulfuric acid solution is added slowly until two clear phases are obtained. After separation of the phases by settling, the aqueous phase is extracted with ethyl ether (3×100 ml).

After evaporation of the solvent under reduced pressure, the crude product is purified by chromatography on a column of silica and eluted with mixtures consisting of pentane and ethyl ether of increasing polarity (100:0 to 80:20). The 1-(2,2'-bithien-5-yl)-3,4-dihydro-6-methoxynaphthalene is isolated in the form of an oil.

Yield: 60%

Empirical formula: $C_{19}H_{16}OS_2$

Molar mass: 324.467 g.

Step 5

27 mmol of chloranil and 50 ml of anhydrous benzene are introduced into a 250 ml 2-necked flask fitted with a stirring system and over which is mounted a condenser. The reaction takes place under argon. 9.2 mmol of the cycloalkene obtained in Step 4, dissolved beforehand in 20 ml of benzene, are added dropwise using a dropping funnel, and the reaction mixture is then maintained at the reflux point of the solvent for 5 hours. The cooled solution is filtered under vacuum through silica and is eluted rapidly with ethyl ether. After evaporation of the solvent under reduced pressure, the crude product is purified by chromatography on a column of silica and eluted with mixtures consisting of pentane and ethyl ether of increasing polarity (100:0 to 80:20).

The residual oily compound is 1-(2,2'-bithien-5-yl)-6-methoxynaphthalene.

Yield: 93%

Empirical formula: $C_{19}H_{14}OS_2$

Molar mass: 422.451 g.

Step 6

8.6 mmol of the compound obtained in Step 5 and 15 ml of pre-distilled $CH_2Cl_2$ are introduced into a 50 ml 3-necked flask fitted with a stirring system and over which is mounted a condenser. The reaction mixture is cooled to 0° C., after which 11.2 ml (11 mmol) of a 1M solution of $BBr_3$ in $CH_2Cl_2$ are added. The addition lasts about 20 minutes. The reaction is carried out under argon. The mixture is then heated at the reflux point of the $CH_2Cl_2$ for 15 hours. The reaction mixture is allowed to return to room temperature and is then neutralized with saturated $Na_2CO_3$ solution until a pH equal to 7 is obtained. The mixture obtained is filtered through Celite. After separation of the phases by settling, the aqueous phase is extracted with $CH_2Cl_2$ (3×10 ml). The organic phases are combined, washed with water and then dried over magnesium sulfate. After evaporation of the solvent under reduced pressure, the crude product is purified by chromatography on a column of silica and eluted with mixtures consisting of pentane and ethyl ether of increasing polarity (100:0 to 50:50). The 1-(2,2'-bithien-5-yl)-6-hydroxynaphthalene is isolated in a yield of 24%.

Empirical formula: $C_{18}H_{12}OS_2$

Molar mass: 308.424 g

Melting point: 133° C.

Step 7

A mixture consisting of 1 mmol of propargyl alcohol prepared in Step 3, 1 mmol of the naphthol prepared in Step 6 and 20 ml of anhydrous $CH_2Cl_2$ is stirred under argon.

A catalytic amount of pyridinium paratolueuesulfonate is added at room temperature. The reaction mixture is left stirring for 6 to 8 hours. The reaction is monitored by analytical thin layer chromatography. The mixture is poured into ice-cold 5% sodium hydroxide solution. The aqueous phase is extracted three times with dichloromethane. The combined organic phases are dried over magnesium sulfate and are then concentrated under reduced pressure. The residue is purified by chromatography on a column of silica with pentane/dichloromethane mixtures of increasing polarity (100:0 to 50:50). The 3,7-bis(2,2'-bithien-5-yl)-3-(2-thienyl)[3H]naphtho[2,1-b]pyran is isolated in a yield of 30%.

Empirical formula: $C_{33}H_{20}OS_5$

Melting point: 98° C.

EXAMPLE 2

Synthesis of 3,8-bis(2,2'-bithien-5-yl)-3-(4-methoxyphenyl)[3H]naphtho[2,1-b]pyran

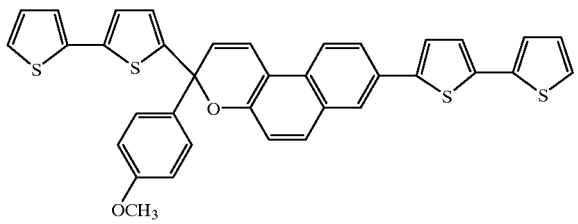

Step 1

(2,2'-Bithien-5-yl)(4-methoxyphenyl) ketone is prepared according to the same procedure as that described in Step 2 of Example 1. The precursors in this case are 4-methoxybenzoyl chloride and 2,2-bithiophene.

Yield: 85%
Empirical formula: $C_{16}H_{12}O_2S_2$
Molar mass: 300.402 g
Melting point: 119–120° C.

Step 2

1-(2,2'-Bithien-5-yl)-1-(4-methoxyphenyl)-2-propyn-1-ol is prepared according to the same procedure as that described in Step 3 of Example 1. The precursor in this case is the ketone described above (Step 1, Example 2).

Yield: 87%
Empirical formula: $C_{18}H_{14}O_2S_2$
Molar mass: 326.441 g
Oily product.

Step 3

6 mmol of 2,2'-bithiophene diluted in 30 ml of anhydrous THF are introduced into a 3-necked round-bottomed flask under argon. The mixture is cooled to −40° C. 2.65 ml (1.05 mmol) of a 2.5M solution of nBuLi in hexane are then added slowly. The resulting mixture is stirred for 1 hour at −40° C. and then cooled to −90° C. 4 ml (18 mmol) of $B(OBu)_3$ are then added as quickly as possible. The mixture is allowed to return to room temperature and 30 mmol of 2,2-dimethylpropane-1,3-diol are then added. The resulting mixture is stirred for 10 minutes and then hydrolyzed with 30 ml of water. The water-THF mixture is extracted with benzene (3×30 ml). The resulting organic phase is washed several times with saturated aqueous NaCl solution, dried over magnesium sulfate and then concentrated under reduced pressure. The crude product chromatographed on a column of silica, eluted with pentane/dichloromethane mixtures of increasing polarity (100:0 to 70:30), gives 5,5-dimethyl-2-(2,2'-bithien-2-yl)[1,3,2]dioxoborinane.

Yield: 46%
Empirical formula: $C_{13}H_{25}O_2S_2B$
Molar mass: 278.20 g.

Step 4

A mixture of 3.59 mmol of the boronic ester prepared in Step 3 (Example 1), 3 mmol of 6-bromo-2-hydroxynaphthalene, 4.5 mmol of $K_3PO_4$, a catalytic amount of Pd $(PPh_3)_4$ and 9 ml of DMF is maintained at 100° C. for 24 hours. The reaction mixture is allowed to return to room temperature and is then diluted with 20 ml of THF. The solution is filtered through Celite. The THF is evaporated off under reduced pressure. On addition of water, the organic products precipitate. The mixture is filtered and the resulting solid is recrystallized from a heptane/THF mixture.

2-(2,2'-Bithien-5-yl)-6-hydroxynaphthalene is obtained in a yield of 78%.

Empirical formula: $C_{18}H_{12}OS_2$
Molar mass: 308.329 g
Melting point: 231° C.

Step 5

3,8-Bis(2,2'-bithien-5-yl)-3-(4-methoxyphenyl)[3H]naphtho[2,1-b]pyran is obtained according to the procedure described in Step 7 of Example 1. The precursors in this case are the propargyl alcohol and the naphthol respectively described in Steps 2 and 4 of Example 2. The final product is recrystallized from toluene.

Yield: 72%
Empirical formula: $C_{36}H_{24}O_2S_4$
Molar mass: 616.658 g
Melting point: 210° C.

EXAMPLE 3

Synthesis of 3,8-bis(2,2'-bithien-5-yl)-3-(2-thienyl)[3H]naphtho[2,1-b]pyran

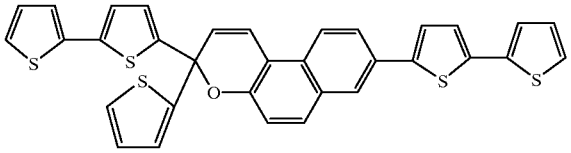

Step 1

(2,2'-Bithien-5-yl)(2-thienyl)ketone is obtained from 2-thiophene carboxylic acid chloride and 2,2'-biothiophene according to the procedure of Step 2 of Example 1.

Yield: 83%
Empirical formula: $C_{13}H_8OS_4$
Molar mass: 276.404 g
Melting point: 98° C.

Step 2

1-(2,2'-Bithien-5-yl)-1-(2-thienyl)-2-propyn-1-ol is obtained from the ketone described in Step 1 (Example 3) according to the procedure described in Step 3 of Example 1.

Yield: 81%
Empirical formula: $C_{35}H_{10}OS_3$
Molar mass: 302.441 g
Oily product.

Step 3

3,8-Bis(2,2'-bithien-5-yl)-3-(2-thienyl)[3H]-naphtho[2,1-b]pyran is obtained according to the procedure described in Step 7 of Example 1. The precursors in this case are the propargyl alcohol described in Step 2 above (Example 3) and the naphthol described in Step 4 of Example 2. The final product is recrystallized from toluene.

Yield: 67%

Empirical formula: $C_{33}H_{20}OS_5$

Molar mass: 592.692 g

Melting point: 213° C.

EXAMPLE 4

Synthesis of 3,8-bis(2,2'-bithien-5-yl)-3-(4-pentyloxyphenyl)[3H]naphtho[2,1-b]pyran

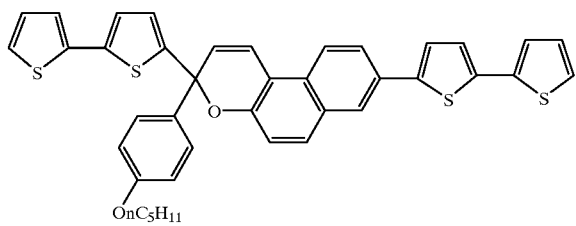

Step 1

(2,2'-Bithien-5-yl)(4-pentyloxyphenyl)ketone is obtained from 4-pentyloxybenzoyl chloride and 2,2'-bithiophene according to the procedure of Step 2 of Example 1.

Yield: 93%

Empirical formula: $C_{20}H_{20}O_2S_2$

Molar mass: 356.350 g

Melting point: 114° C.

Step 2

1-(2,2'-Bithien-5-yl)-1-(4-pentyloxyphenyl)-2-propyn-1-ol is obtained from the ketone described in Step 1 (Example 5) according to the procedure described in Step 3 of Example 1.

Yield: 81%

Empirical formula: $C_{15}H_{10}S_3$

Molar mass: 302.441 g

Oily product.

Step 3

3,8-Bis(2,2'-bithien-5-yl)-3-(4-pentyloxyphenyl)[3H]naphtho[2,1-b]pyran is obtained according to the procedure described in Step 7 of Example 1. The precursors in this case are the propargyl alcohol described in Step 2 above (Example 4) and the naphthol described in Step 4 of Example 2. The final product is recrystallized from heptane.

Yield: 78%

Empirical formula: $C_{40}H_{32}O_2S_4$

Molar mass: 672.702

Melting point: 147° C.

EXAMPLE 5

Synthesis of 3,3,8-tris(2,2'-bithien-5-yl)[3H]naphtho[2,1-b]pyran

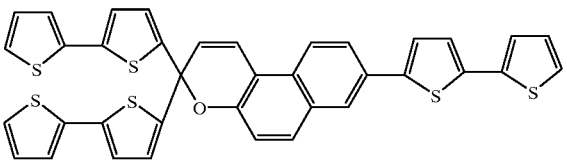

Step 1

Bis(2,2'-bithien-5-yl)ketone is obtained from 5-(2'-thienyl)-2-thenoyl chloride and 2,2'-bithiophene according to the procedure of Step 2 of Example 1. The purification is carried out by chromatography on a column of silica using pentane/$CH_2Cl_2$ mixtures of increasing polarity (0:100 to 50:50) as eluent. Recrystallization is carried out in benzene.

Yield: 66%

Empirical formula: $C_{17}H_{10}OS_4$

Molar mass: 358.450 g

Melting point: 181° C.

Step 2

1-Bis(2,2'-bithien-5-yl)-2-propyn-1-ol [sic] is obtained from the ketone described in Step 1 (Example 5) according to the procedure described in Step 3 of Example 1. It is used without purification for the next step, since chromatography on silica or alumina degrades this compound.

Empirical formula: $C_{19}H_{12}OS_4$

Molar mass: 384.472 g

Oily product.

Step 3

3,3,8-Tris(2,2'-bithien-5-yl)[3H]naphtho[2,1-b]pyran is obtained according to the procedure described in Step 7 of Example 1. The precursors in this case are the propargyl alcohol described in Step 2 above (Example 5) and the naphthol described in Step 4 of Example 2. The final product is recrystallized from toluene.

Yield: 44% (Step 2+Step 3)

Empirical formula: $C_{37}H_{22}OS_6$

Molar mass: 674.802 g

Melting point: 223° C.

EXAMPLE 6

Synthesis of 3,8-bis(2,2'-bithien-5-yl)-3-(5-methoxy-2-thienyl)[3H]naphtho[2,1-b]pyran

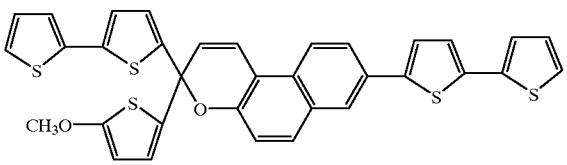

Step 1

(2,2'-Bithien-5-yl)(5-methoxy-2-thienyl)ketone is obtained from 5-methoxythenoyl chloride and 2,2'- bithiophene according to the procedure of Step 2 of Example 1. The purification is carried out by chromatography on a column of silica using pentane/CH$_2$Cl$_2$ mixtures of increasing polarity as eluents.

Yield: 72%
Empirical formula: C$_{14}$H$_{10}$O$_2$S$_3$
Molar mass: 306.350 g
Melting point: 106° C.

Step 2

1-(2,2'-Bithien-5-yl)-1-(5-methoxy-2-thienyl)-2-propyn-1-ol is obtained from the ketone described in Step 1 (Example 6) according to the procedure described in Step 3 of Example 1. It is used without purification for the following step, since chromatography on silica degrades the compound.

Empirical formula: C$_{16}$H$_{12}$O$_2$S$_3$
Molar mass: 322.374 g
Oily product.

Step 3

3,8-Bis(2,2'-bithien-5-yl)-3-(5-methoxy-2-thienyl)[3H]naphtho[2,1-b]pyran is obtained according to the procedure described in Step 7 of Example 1. The precursors in this case are the propargyl alcohol described in Step 2 (Example 6) and the naphthol described in Step 4 of Example 2. The final product is recrystallized from toluene.

Yield: 52% (Step 2+Step 3)
Empirical formula: C$_{34}$H$_{22}$O$_2$S$_5$
Molar mass: 622.702 g
Melting point: 204° C.

EXAMPLE 7

Synthesis of 3,8-bis(2,2'-bithien-5-yl)-3-(4-pentyloxyphenyl)-3-(2,2'-5',2''-terthien-5-yl)[3H]naphtho[2,1-b]pyran [sic]

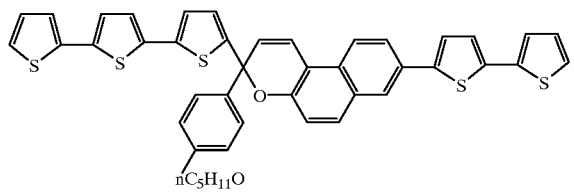

Step 1

(4-Pentyloxyphenyl)(2,2'-5',2''-terthien-5-yl)ketone is obtained from 4-pentyloxybenzoyl chloride and 2,2'-5',2''-terthiophene according to the procedure of Step 2 of Example 1. The purification is carried out by chromatography on a column of silica using pentane/CH$_2$Cl$_2$ mixtures of increasing polarity as eluents.

Yield: 53%
Empirical formula: C$_{24}$H$_{22}$O$_2$S$_3$
Molar mass: 438.460 g
Melting point: 174° C.

Step 2

1-(4-Pentyloxyphenyl)-1-(2,2'-5',2''-terthien-2-yl)-2-propyn-1-ol is obtained from the ketone described in Step 1 (Example 7) according to the procedure described in Step 3 of Example 1.

Yield: 73%
Empirical formula: C$_{27}$H$_{24}$O$_2$S$_3$
Molar mass: 478.275 g
Oily product.

Step 3

8-(2,2'-Bithien-5-yl)-3-(4-pentyloxyphenyl)-3-(2,2'-5',2''-terthien-5-yl)[3H]naphtho[2,1-b]pyran is obtained according to the procedure described in Step 7 of Example 1. The precursors in this case are the propargyl alcohol described in Step 2 above (Example 7) and the naphthol described in Step 4 of Example 2. The final product is recrystallized from toluene.

Yield: 63%
Empirical formula: C$_{44}$H$_{35}$O$_2$S$_5$
Molar mass: 755.812 g
Melting point: 158° C.

EXAMPLE 8

Synthesis of 3,5-bis(2,2'-bithien-5-yl-3-(4pentyloxyphenyl)[3H]naphtho[2,1-b]pyran [sic]

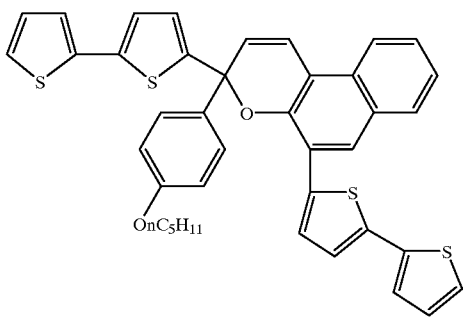

Step 1

(2,2'-Bithien-5-yl) 4-pentyloxyphenyl ketone was obtained according to the same procedure as that described for Step 1 of Example 3.

Step 2

1-(2,2'-Bithien-5-yl)-1-(4-pentyloxyphenyl)-2-propyn-1-ol was obtained according to the same procedure as that described for Step 2 of Example 3.

Step 3

12 mmol of dihydroxynaphthalene and 25 ml of pyridine are stirred under argon at room temperature for 20 minutes. The mixture is cooled to 0° C. and 2.1 ml (12 mmol) of trifluoromethane sulfonic anhydride are introduced slowly.

The mixture is allowed to return to room temperature and is stirred overnight. The solution is then poured into ice-water (25 ml) and then extracted with ethyl ether (3×30 ml). The resulting organic phase is washed with water (2×20 ml) and then with saturated aqueous saline solution (20 ml). The organic phase is dried over magnesium sulfate. After evaporation under reduced pressure, a brown oil is isolated. The crude product is chromatographed on a column of silica eluted with pentane/ether mixtures of increasing polarity (100/0 to 70/30) to give 2-hydroxy-3-trifluoromethane sulfonatonaphthalene.

Yield: 20%
Empirical formula: $C_{11}H_7O_3SF_3$
Molar mass: 292.230 g
Melting point: 62–630C.

Step 4

5,5'-Dimethyl-2-(2,2'-bithien-2-yl) [1,3,2]dioxoborinane is prepared according to the procedure of Step 3 of Example 2.

Step 5

2-(2,2'-Bithien-5-yl)-3-hydroxynaphthalene is obtained according to the same experimental procedure as that described in Step 4 of Example 2.

11.34 mmol of the boronic ester (Step 4 above), 9.45 mmol of the naphthol prepared in Step 3 above, 14.17 mmol of $K_3PO_4$, a catalytic amount of $Pd(PPh_3)_4$ and 13 ml of DMF are used in this case.

Yield: 74%
Empirical formula: $C_{18}H_{12}OS_2$
Molar mass: 308.329 g
Melting point: 174° C.

Step 6

3,5-Bis (2,2'-bithien-5-yl)-3-(4-pentyloxyphenyl)[3H]naphtho[2,1-b]pyran is obtained according to the procedure described in Step 7 of Example 1.

The precursors in this case are the propargyl alcohol and the naphthol described respectively in Steps 2 and 5 of this Example 8.

Yield: 76%
Empirical formula: $C_{40}H_{32}O_2S_4$
Molar mass: 672.702 g
Melting point: 77° C.

Comparative Example 1

3,3-Diphenyl[3H]naphtho[2,1-b]pyran is prepared in the following way:

10 mmol of 1,1-diphenyl-2-propyn-1-ol and 11 mmol of 2-naphthol are dissolved in warm anhydrous toluene (20 ml). A catalytic amount of para-toluene sulfonic acid is added. The mixture is refluxed under argon for 2 h 30 minutes. It is allowed to cool to room temperature and 20 ml of aqueous 5% NaOH solution are added. The aqueous phase is extracted continuously with methylene chloride. The organic phases are combined and dried over magnesium sulfate. The solvent is evaporated off under reduced pressure. The resulting product is purified by washing with hexane.

Yield: 62%
Empirical formula: $C_{24}H_{18}O$
Molar mass: 334.42 g
Melting point: 158° C.

Comparative Example 2

3,3-Bis(4-methoxyphenyl)[3H]naphtho[2,1-b]pyran is prepared in the following way:

The procedure is identical to the one used in Comparative Example 2, the precursor in this case being 1,1-bis(4-methoxyphenyl)-2-propyn-1-ol.

EXAMPLE 9

$10^{-4}$ M solutions in toluene of the photochromic compounds obtained in the examples and the comparative examples were prepared.

The photochromic properties were determined at 20° C. on a Beckman DU 700 electron absorption spectrophotometer. An external irradiation, perpendicular to the analysis beam, was provided by a 150 W Xenon arc lamp equipped with a water filter, a diaphragm and a light guide. The luminous flux was kept constant for all the recordings.

In a first experiment, the absorption spectrum of the colored form obtained after irradiation for 2 minutes was recorded in order to determine the maximum absorption wavelength in the visible range ($\lambda$max).

In a second experiment, the variation in the absorbence of the solution at the $\lambda$max of absorption as a function of the irradiation time was recorded, and the maximum absorbence obtained after a few seconds to a few tens of seconds of irradiation was measured (A$\infty$). The irradiation was then stopped. The decrease in absorbence as a function of time was then recorded, thus allowing the thermal decolorization constant (k$\Delta$) to be evaluated.

The results are given in Table I below.

TABLE I

| Toluene solvent, T = 20° C. | (A $\infty$) | k$\Delta$ (s$^{-1}$) | $\lambda$max (nm) |
| --- | --- | --- | --- |
| Example 1 | 0.15 | 0.60 | 520 |
| Example 2 | 0.43 | 0.19 | 549 |
| Example 3 | 0.36 | 0.18 | 549 |
| Example 4 | 0.38 | 9.19 | 548 |
| Example 5 | 0.35 | 0.29 | 564 |
| Example 6 | 0.21 | 0.55 | 560 |
| Example 7 | 0.50 | 0.19 | 564 |
| Comp. Example 1 | 0.23 | 0.06 | 432 |
| Comp. Example 2 | 0.13 | 0.24 | 480 |

The results show that the photochromic compounds according to the invention have a maximum absorption wavelength ($\lambda$max) which is very substantially shifted towards higher wavelengths (bathochromic shift) and an absorbance maximum which is higher than that of the compounds in the comparative examples.

EXAMPLE 10

$10^{-4}$ M toluene solutions of the photochromic compounds obtained in Example 2 and in Comparative Example 1 were irradiated under the conditions of Example 9. This time, the coloration times (time required to reach the photostationary equilibrium) and the percentage of decolorization at 10 sec after the end of the irradiation were measured.

|  | Coloration | Decolorization |
| --- | --- | --- |
| Compound | Time required to reach the photostationary equilibrium (s) | % of decolorization at 10 s |
| Example 2 | 14 | 83% |
| Comp. Example 1 | 26 | 50% |

EXAMPLE 11

$10^{-4}$ M toluene solutions of the photochromic compounds obtained in Example 2 and in Comparative Example 1 were irradiated under the conditions of Example 9, but with a GG400 filter (Schott), which cuts out all the UV radiation with a wavelength of less than 380 nm, being placed in the light beam.

Whereas the solution prepared from Comparative Example 1 does not develop a coloration, the solution prepared from the compound of Example 2 maintains photochromic properties.

EXAMPLE 12

A polyurethane film (15 µm thick) containing 2×10⁻⁵ ml/g of the naphthopyran of Example 2 was prepared. Under the same irradiation conditions as those described in Example 8, this sample showed excellent photochromic properties:

A∞=0.1, λmax=344 nm, k=0.14 s⁻¹.

Although slower than the toluene solution of Example 8, the decolorization speed is still very fast.

What is claimed is:

1. A photochromic compound having a [3H]naphtho-[2,1-b]pyran structure and comprising at least one substituted or unsubstituted bithienyl group in one of the positions 5–10 of the naphthalene ring system of said structure and at least one substituted or unsubstituted bithienyl or terthienyl group in position 3 of said structure.

2. The photochromic compound of claim 1, further defined as having a formula:

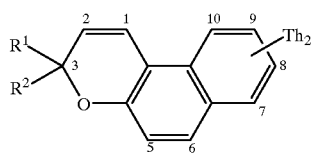

(I)

in which the Th₂ group represents a bithienyl group in one of the positions 5 to 10 of the naphthenic ring system and corresponds to the formula:

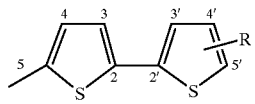

(II)

in which:

R denotes a substitutent in one of the positions 3, 3', 4, 4' or 5', chosen from a hydrogen atom, an alkyl group, a cycloalkyl group, an aryl group, a group OR³, SR³, COR³ and COOR³, in which R³ denotes a hydrogen atom, an alkyl group, an aryl group, an amino group, an NO₂, CN or SCN group, a halogen atom or a mono- or polyhaloalkyl group;

R¹ denotes a Th₂ group as defined above or a Th₃ group of formula:

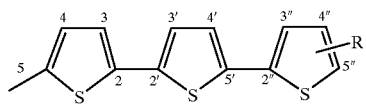

(III)

in which

R is a substituent as denoted above which can occupy one of the positions 3, 3', 3", 4, 4', 4", and 5"; and R² denotes a Th₂ group, a Th₃ group, an aryl group, a naththyl group, a thienyl group, a furyl group, a pyrrolyl group or an N-alkylpyrrolyl group.

3. The photochromic compound of claim 2, wherein the alkyl groups are C₅–C₇ cycloalkyl groups, the aryl groups comprise phenyl and (C₁–C₆)alkylphenyl, and the halogens are bromine, chlorine and fluorine.

4. The photochromic compound of claim 2, wherein, in the Th₂ group, the substituent R is in position 5'.

5. The photochromic compound of claim 2, wherein, in the Th₃ group, the substituent R is in position 5".

6. The photochromic compound of claim 2, wherein the Th₂ group is in position 8 of the naphthalene ring system.

7. The photochromic compound of claim 2, wherein R¹ is a Th₃ group.

8. A process for preparing a photochromic compound having a formula:

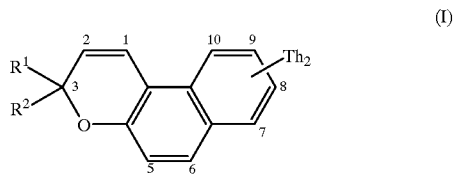

(I)

in which the Th₂ group represents a bithienyl group in one of the positions 5 to 10 of the naphthenic ring system and corresponds to the formula:

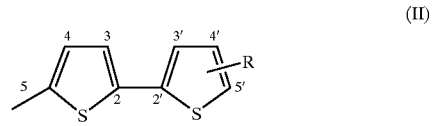

(II)

in which:

R denotes a substituent in one of the positions 3, 3', 4, 4' or 5', chosen from a hydrogen atom, an alkyl group, a cycloalkyl group, an aryl group, a group OR³, SR³, COR³ and COOR³, in which R³ denotes a hydrogen atom, an alkyl group, an aryl group, an amino group, an NO₂, CN or SCN group, a halogen atom or a mono- or polyhaloalkyl group;

R¹ denotes a Th₂ group as defined above or a Th₃ group of formula:

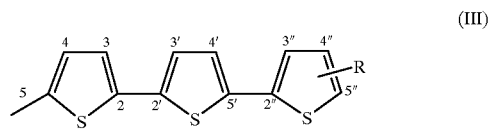

(III)

in which

R is a substituent as denoted above which can occupy one of the positions 3, 3', 3", 4, 4', 4", and 5"; and R² denotes a Th₂ group, a Th₃ group, an aryl group, a naththyl group, a thienyl group, a furyl group, a pyrrolyl group or an N-alkylpyrrolyl group, the process comprising reacting, in the presence of an acid catalyst, a propargyl alcohol of formula:

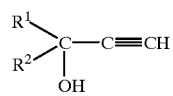

(A)

in which R¹ denotes a Th₂ group as defined above or a Th₃ group as defined above; with a 2-naphthol of formula:

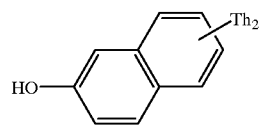 (B)

in which Th$_2$ is as defined above.

9. A transparent article comprising a substrate made of transparent polymer material, in which at least one photochromic compound having a [3H]naphtho-[2, 1-b]pyran structure and comprising at least one substituted or unsubstituted bithienyl group in one of the positions 5–10 of the naphthalene ring system of said structure and at least one substituted or unsubstituted bithienyl or terthienyl group in position 3 of said structure, is incorporated into the substrate.

10. A transparent article comprising a substrate made of transparent polymer material, in which at least one face of the article is coated with a film made of transparent polymer material incorporating at least one photochromic compound having a [3H]naphtho[2,1-b]-pyran structure and comprising at least one substituted or unsubstituted bithienyl group in one of the positions 5–10 of the naphthalene ring system of said structure and at least one substituted or unsubstituted bithienyl or terthienyl group in position 3 of said structure.

11. The article of claim 9, in which the article is further defined as glazing for the construction industry, a motor vehicle or airplane windshield, a helmet visor or a spectacle glass.

12. The article of claim 10, in which the article is further defined as glazing for the construction industry, a motor vehicle or airplane windshield, a helmet visor or a spectacle glass.

* * * * *